United States Patent [19]

Shim

[11] 4,456,539

[45] Jun. 26, 1984

[54] TRIAZOLE-DITHIOPHOSPHATE REACTION PRODUCT AND LUBRICANT COMPOSITIONS CONTAINING SAME

[75] Inventor: Joosup Shim, Wenonah, N.J.

[73] Assignee: Mobil Oil Corporation, New York, N.Y.

[21] Appl. No.: 402,877

[22] Filed: Jul. 29, 1982

[51] Int. Cl.³ ............................................. C10M 1/48
[52] U.S. Cl. ................................. 252/46.7; 252/49.5; 260/429.9; 548/256; 548/259
[58] Field of Search ............... 252/46.7, 32.7 E, 49.5; 548/256, 259; 260/429.9

[56] References Cited

U.S. PATENT DOCUMENTS

| | | | |
|---|---|---|---|
| 2,706,194 | 4/1955 | Morris et al. | 252/46.7 X |
| 3,192,162 | 6/1965 | Bartlett et al. | 252/46.7 X |
| 3,813,336 | 5/1974 | Goldschmidt | 252/32.7 E |
| 3,846,317 | 11/1974 | Lintzenich | 252/46.7 |
| 4,298,481 | 11/1981 | Clarke | 252/21 |
| 4,306,984 | 12/1981 | Yamaguchi | 252/46.7 |

FOREIGN PATENT DOCUMENTS 737287 9/1955 United Kingdom ............... 252/46.7

*Primary Examiner*—Andrew Metz
*Attorney, Agent, or Firm*—Alexander J. McKillop; Michael G. Gilman; Claude E. Setliff

[57] ABSTRACT

Oxidation in lubricants is reduced by adding to the lubricant a small portion of a triazole/dithiophosphate reaction product.

27 Claims, No Drawings

TRIAZOLE-DITHIOPHOSPHATE REACTION PRODUCT AND LUBRICANT COMPOSITIONS CONTAINING SAME

BACKGROUND OF THE INVENTION

1. Field of the Invention

This invention relates to the inhibition of oxidation in lubricants. More particularly, the invention has to do with lubricants in which have been placed an additive having the ability to reduce oxidation of such luricant. Still more particularly, the additive of this invention is a reaction product made by reacting a benzotriazole with a metal dihydrocarbyl dithiophosphate.

2. Discussion of the Prior Art

Lubricants, such as lubricating oils and greases, are subject to oxidative deterioration at elevated temperatures or upon prolonged exposure to the elements. Such deterioration is evidenced, in many instances, by an increase in acidity and in viscosity, and when the deterioration is severe enough, it can cause metal parts to corrode. Additionally, severe oxidation eeads to a loss of lubrication properties of the lubricants, and, in especially severe cases, to complete breakdown of the device being lubricated. In combatting oxidation, many additives have been tried, but many of them are only marginally effective except at high concentrations, especially when the lubricant is subjected to drastic oxidizing conditions.

Antioxidants or oxidation inhibitors are used to minimize the effects of oil deterioration that will occur whenever hot oil is contacted with air. The degree and rate of oxidation will depend on temperature, air and oil flow rates and, of particular importance, on the presence of metals that may catalytically promote oxidation.

Antioxidants generally function by prevention of chain peroxide reaction and/or metal catalyst deactivation. They prevent the formation of acid sludges, darkening of the oil and increases in viscosity due to the formation of polymeric materials.

Typical prior art lubricant antioxidants are hindered phenolic compounds such as 2,6-di-tert-butyl-4-methyl phenol commonly known as DBPC in lubricants and BHT in foods. On occasion, these phenolic compounds are combined with amine antioxidants for optimum activity; however, amines generally cannot be used alone as lubricant antioxidants due to their tendency to decompose and form sludge.

Applicant does not know of any prior practices embracing or suggesting the product disclosed herein or its use in a lubricant. The closest prior disclosures of which he is aware are U.S. Pat. No. 3,986,967 and U.S. Pat. No. 4,298,481. The former discloses compounds of the formula

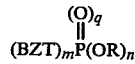

where BZT is benzotriazole, q is 0 or 1, m is 1 or 2 and n is 1 or 2, the sum of m and n being 3. These are used as load carrying agents in lubricants. The latter patent discloses a grease formulation containing many additives, among those suggested as possible being alkylbenzotriazole and a Group II metal diorganodithiophosphate. It should be observed that these two components of the latter patent are not reacted in the patented grease composition.

SUMMARY OF THE INVENTION

In accordance with the invention, there is provided a product of reaction obtained by reacting an alkylbenzotriazole with an organodithiophosphate salt. The invention also provides a lubricant composition comprising a major amount of a lubricant and an antioxidant amount of the said product of reaction.

DISCUSSION OF SPECIFIC EMBODIMENTS

The alkylbenzotriazoles useful in the practice of this invention have the formula

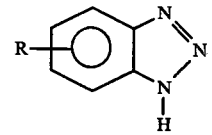

wherein R is an alkyl group having 1 to 12 carbon atoms, including methyl, ethyl, butyl, hexyl, octyl, nonyl, decyl and dodecyl groups. A specific member embraced is tolutriazole (where R is methyl). These are readily available from commercial sources or are easily made using known prior art methods.

The organodithiophosphates used to prepare the products of the invention have the formula

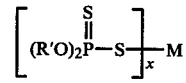

where R′, which may be the same or different, is a hydrocarbyl group, preferably an alkyl group or an alkaryl group, containing 1 to 25 carbo atoms, M is a cation which includes the ammonium ion or a metal, preferably from Groups IA, IIA, IIB, VIB and VII, and x is the valence of M. Specific useful members include sodium, calcium, zinc, chromium, iron, nickel and cobalt. "Ammonium" used herein means an $NH_4^+$ cation or an ammonium cation containing 1 to 4 hydrocarbyl groups.

The phosphorodithioic acids used to prepare the metal salts are generally prepared by reacting a suitable phosphorus sulfide, e.g., phosphorus pentasulfide, with a variety of phenolic or alcoholic materials, preferably a hydroxylic compound R′OH where, as mentioned above, R′ may have up to 25 carbon atoms. A non-exhaustive list of suitable hydroxylic compounds include phenol, alkyl-substituted phenol, wherein the alkyl group contains 1 to 19 carbon atoms, methanol, ethanol, n-propanol, i-propanol, n-butanol, i-butanol, dimethyl butanol, primary and secondary pentanols, hexanol, ethylhexanol, eicosanol and mixtures thereof.

The preparation of the phosphorodithioic acids may be carried out in any convenient manner known to the art. These acids may also be obtained commercially or made, for example, by slowly reacting a mixture of phosphorus sulfide, e.g., pentasulfide, and the aforementioned hydroxylic component under suitable reaction conditions.

The reaction between the phosphorodithioic acid salt and triazole compound is carried out at temperatures of from about 70° C. to about 150° C., preferably about 90°

C. to about 110° C. for from about 1 to about 10 hours, or preferably from about 2 to about 4 hours. Desirable solvents which can be used include hydrocarbon solvents such as hexane, benzene, toluene and the like, or alcoholic solvents such as methanol, ethanol, propanol, isopropanol and butanol.

The reactants are preferably used in equimolar quantities, but an excess of either may be used, if desired.

The reaction products are used with lubricants to the extent of from about 0.1% to about 10% by weight of the total composition. Furthermore, other additives, such as detergents, anti-wear agents and the like may be present. These can include phenates, sulfonates, succinimides, polymers, calcium and magnesium salts and the like.

The lubricants contemplated for use with the compounds herein disclosed include mineral and synthetic hydrocarbon oils of lubricating viscosity, mixtures of mineral oils and synthetic oils and greases from any of these, including mixtures. The synthetic hydrocarbon oils include long-chain alkanes such as cetanes and olefin polymers such as oligomers of hexane, octane, decene, and dodecane, etc. These vicinal diols are especially effective in synthetic oils formulated using mixtures of synthetic hydrocarbon olefin oligomers and lesser amounts of hydrocarbyl carboxylate ester fluids. The other synthetic oils, which can be used alone with the borated compounds of this invention, or which can be mixed with a mineral or synthetic hydrocarbon oil, include (1) fully esterified ester oils, with no free hydroxyls, such as pentaerythritol esters of mono-carboxylic acids having 2 to 20 carbon atoms, trimethylolpropane esters of monocarboxylic acids having 2 to 20 carbon atoms, (2) polyacetals and (3) siloxane fluids. Especially useful among the synthetic esters are those made from polycarboxylic acids and monohydric alcohols. More preferred are the ester fluids made by fully esterifying pentaerythritol, or mixtures thereof with di- and tripentaerythritol, with an aliphatic mono-carboxylic acid containing from 1 to 20 carbon atoms, or mixtures of such acids.

A wide variety of thickening agents can be used in the greases of this invention. Included among the thickening agents are alkali and alkaline earth metal soaps of fatty acids and fatty materials having from about 12 to about 30 carbon atoms per molecule. The metals are typified by sodium, lithium, calcium and barium. Fatty materials are illustrated by stearic acid, hydroxystearic acid, stearin, cottonseed oil acids, oleic acid, palmitic acid, myristic acid and hydrogenated fish oils.

Other thickening agents include salt and salt-soap complexes as calcium stearate-acetate (U.S. Pat. No. 2,197,263), barium stearate acetate (U.S. Pat. No. 2,564,561), calcium stearate-caprylate-acetate complexes (U.S. Pat. No. 2,999,065), calcium-caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline.

The preferred thickening gelling agents employed in the grease compositions are essentially hydrophobic clays. Such thickening agents can be prepared from clays which are initially hydrophilic in character, but which have been converted into a hydrophobic condition by the introduction of long chain hydrocarbon radicals into the surface of the clay particles; prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. This method of conversion, being well known to those skilled in the art, is believed to require no further discussion, and does not form a part of the present invention. More specifically, the clays which are useful as starting materials in forming the thickening agents to be employed in the grease compositions, can comprise the naturally occurring chemically unmodified clays. These clays are crystalline complex silicates, the exact composition of which is not subject to precise description, since they vary widely from one natural source to another. These clays can be described as complex inorganic silicates such as aluminum silicates, magnesium silicates, barium silicates, and the like, containing, in addition to the silicate lattice, varying amounts of cation-exchangeable groups such as sodium. Hydrophilic clays which are particularly useful for conversion to desired thickening agents include montmorillonite clays, such as bentonite, attapulgite, hectorite, illite, saponite, sepiolite, biotite, vermiculite, zeolite clays, and the like. The thickening agent is employed in an amount from about 0.5 to about 30, and preferably from 3 percent to 15, percent by weight of the total grease composition.

Having described the invention in general terms, the following are offered to specifically illustrate the development. It is to be understood they are illustrations only and that the invention shall not be limited except as limited by the appended claims.

EXAMPLE 1

A mixture of 50 grams of tolutriazole and 450 grams of zinc di(dodecylphenyl) dithiophosphate was gradually heated to a temperature of 95° C. with stirring. After the resulting mixture had been stirred at the temperature for a period of one hour, the resulting reaction product became quite clear and the reaction was immediately discontinued. The reaction product was cooled to room temperature with continuous stirring. The final product was clear and very viscous at room temperature.

EXAMPLE 2

The same method was used with a mixture of tolutriazole and zinc di(1,3-dimethylbutylphenyl)dithiophosphate. This mixture yielded a similar product.

EVALUATION OF PRODUCTS

Emulsion Stability Test

The sample was emulsified and maintained at 200° F. until separation was noted.

V-104C Vane Pump Test (Modified ASTM D2882)

The high pressure Vickers Vane Pump Test is for measuring the wear characteristics of hydraulic fluids. In this test, five gallons of hydraulic fluid are circulated through a pump rig for 100 hours, at $1500\pm30$ psi, $1200\pm60$ rpm, and at a temperature of $150\pm3°$ F. Pump parts are inspected and weighed before and after the 100 hour operation. Then, observations are recorded regarding deposit wear, scuffing and scoring of the various parts, and weight loss to the ring and vane in milligrams are reported. High weight losses (higher than 250 mg.) are indicative of poor antiwear protection.

Table 1 summarizes the data from the vane test and the emulsion stability test.

TABLE 1

| | COMPOSITION TESTED, Wt. % | | | |
|---|---|---|---|---|
| | 1 | 2 | 3 | 4 |
| COMPONENTS | | | | |
| Oil[(1)], wt. % | 100 | 99.60 | 99.60 | 99.60 |
| (2) | — | 0.40 | — | — |
| (3) | — | — | 0.40 | — |
| (4) | — | — | — | 0.40 |
| RESULTS | | | | |
| Emulsion Stability, Days to Separate | 14 | 14[(5)] | 30 | 34 |
| V-104C Vane Pump Test (ASTM D2882) (1500 psi, 150° F., 100 Hr.) Total weight Loss, mg. | 1,679 | 1,600[(5)] | 166 | 56 |

[(1)]Emulsified formulated petroleum based oil containing noted additives.
[(2)]Tolutriazole
[(3)]Didodecylphenyl phosphordithioic acid zinc salt.
[(4)]Reaction product of (1) and (2) [Example 1] in 1:9 weight ratio.
[(5)]Estimated

Rotary Bomb Oxidation Test (ASTM D2272)

The rotary bomb oxidation test (RBOT) represents a rapid means of estimating the oxidation stability of turbine oils. In this method, the test oil, water and copper catalyst coil contained in a glass receptable were placed in a copper bomb equipped with a pressure gauge. The bomb, which was charged with oxygen to a pressure of 90 psi, was placed in a constant temperature oil batch set at 150° F.C. and rotated axially at 100 rpm at an angle of 30 degrees from the horizontal. The time for test oil to react with a given volume of oxygen was measured and reported in minutes. Low RBOT values (less than 100 minutes) are indicative of low or poor oxidation stability.

Catalytic Oxidation

The products were further evaluated for oxidation stabiity. Basically, the test lubricant was subjected to a stream of air bubbled through at the rate of 5 liters per hour at 325° F. for 72 hours. Present in the composion are samples of metals commonly used in engine construction. These include iron, copper, aluminum and lead. U.S. Pat. No. 3,682,980, incorporated herein by reference, has further test details.

Turbine Oil Stability Test (TOST) (Modified ASTM D943)

This method covers the determination of oxidation characteristics of inhibited steam-turbine oils. Briefly, 300 ml of the oil sample is subjected to a temperature of 95° C. in the presence of 60 ml of water, oxygen at a flow rate of 3±0.5 liters/h., and an iron-copper catalyst. At the 1000th hour of the test, the oxidized oil is filtered through a 10 micron filter paper to determine an amount of sludge formed during the test.

The results of these tests are summarized in Table 2.

TABLE 2

| | COMPOSITION (wt. %) | | |
|---|---|---|---|
| | 1 | 2 | 3 |
| COMPONENTS | | | |
| Oil[(1)] | 100 | 99.95 | 99.95 |
| (2) | — | 0.05 | — |
| (3) | — | — | 0.05 |
| RESULTS | | | |
| RBOT, Min. | 360 | 540 | 510 |
| 1000 Hr., TOST, % by wt. | 0.23 | 0.04 | 0.16 |
| CATALYTIC OXIDATION | | | |
| Viscosity Increase, % | 7.82 | 7.95 | 7.84 |
| NN Increase | 5.13 | 5.00 | 4.80 |

[(1)]Formulated petroleum based oil containing dibutyl-p-cresol, p,p'-dioctyldiphenylamine and an amine-succinic compound adduct.
[(2)]Di(1,3-dimethylbutylphenyl) phosphorodithioic acid zinc salt
[(3)]Reaction product of 9 parts of (2) and 1 part of tolutriazole [according to Example 2].

I claim:

1. A product of reaction made by reacting, at a temperature of from about 70° C. to about 150° C., an alkylbenzotriazole with an organodithiophosphate salt, the reactants being used in quantities such that there are present in the reaction mixture equimolar amounts thereof or amounts in which one is in excess of the other.

2. The product of claim 1 wherein the alkylbenzotriazole has the formula:

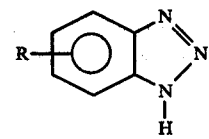

wherein R is an alkyl group having 1 to 12 carbon atoms.

3. The product of claim 2 wherein R is methyl.

4. The product of claim 1 wherein the organodithiophosphate salt has the formula:

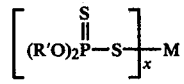

wherein R' is a hydrocarbyl group containing 1 to 25 carbon atoms, M is an ammonium or metal cation and x is the valence of M.

5. The product of claim 4 wherein the hydrocarbyl group is an alkyl group.

6. The product of claim 4 wherein M is a metal cation.

7. The product of claim 6 wherein M is selected from Groups IA, IIA, IIB, VIB and VIII of the Periodic Table.

8. The product of claim 7 wherein the metal is zinc.

9. The product of claim 5 wherein the alkyl group is methyl, ethyl, propyl, butyl, dimethyl butyl, pentyl, hexyl, ethylhexyl or eicosyl.

10. The product of claim 1 wherein the triazole is tolutriazole and the dithiophosphate is zinc di(dodecylphenyl) dithiophosphate.

11. The product of claim 1 wherein the triazole is tolutriazole and the dithiophosphate is zinc di(1,3-dimethylbutylphenyl) dithiophosphate.

12. A lubricant composition comprising a major proportion of a lubricating oil or grease thereof and a minor antioxidant amount of a product of reaction made by reacting, at a temperatuare of from about 70° C. to about 150° C., an alkylbenzotriazole with an organodithiophosphate salt, the reactants being used in quantities such that there are present in the reaction mixture equimolar amounts thereof or amounts in which one is in excess of the other.

13. The composition of claim 12 wherein the alkylbenzatriazole has the formula:

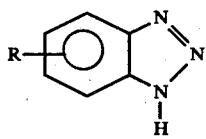

wherein R is an alkyl group having 1 to 12 carbon atoms.

14. The composition of claim 13 wherein R is methyl.

15. The composition of claim 12 wherein the organodithiophosphate salt has the formula:

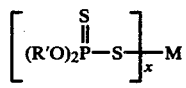

wherein R' is a hydrocarbyl group containing 1 to 25 carbon atoms, M is an ammonium or metal cation and x is the valence of M.

16. The composition of claim 15 wherein the hydrocarbyl group is an alkyl group.

17. The composition of claim 15 wherein M is a metal cation.

18. The composition of claim 17 wherein M is selected from Groups IA, IIA, IIB, VIB and VIII of the Periodic Table.

19. The composition of claim 18 wherein the metal is zinc.

20. The composition of claim 16 wherein the alkyl group is methyl, ethyl, propyl, butyl, dimethyl butyl, pentyl, hexyl, ethylhexyl or eicosyl.

21. The composition of claim 12 wherein the triazole is tolutriazole and the dithiophosphate is zinc di(dodecylphenyl) dithiophosphate.

22. The composition of claim 12 wherein the triazole is tolutriazole and the dithiophosphate is zinc di(1,3-dimethylbutylphenyl) dithiophosphate.

23. The composition of claims 12, 13, 14, 15, 16, 17, 18, 19, 20, 21 or 22 wherein the lubricant is a mineral lubricating oil.

24. The composition of claim 23 wherein the mineral oil is in the form of an emulsion thereof.

25. The composition of claim 12 wherein the lubricant is a grease.

26. The composition of claim 12 wherein the lubricating oil is a synthetic lubricating oil or mixture of synthetic lubricating oils.

27. The composition of claim 12 wherein the lubricating oil is a mixture of (1) mineral lubricating oil and (2) synthetic lubricating oil or mixture of synthetic oils.

* * * * *